US00PP25571P2

(12) United States Plant Patent
Turner

(10) Patent No.: US PP25,571 P2
(45) Date of Patent: May 19, 2015

(54) ***PHORMIUM* PLANT NAMED 'JOKER'**

(50) Latin Name: ***Phormium cookianum*×*Phormium tenax***
Varietal Denomination: Joker

(71) Applicant: Paul Turner, Auckland (NZ)

(72) Inventor: Paul Turner, Auckland (NZ)

( * ) Notice: Subject to any disclaimer, the term of this patent is extended or adjusted under 35 U.S.C. 154(b) by 150 days.

(21) Appl. No.: 13/986,796

(22) Filed: Jun. 5, 2013

Related U.S. Application Data

(60) Provisional application No. 61/689,512, filed on Jun. 7, 2012.

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — Penny J. Aguirre

(57) ABSTRACT

A new cultivar of hybrid *Phormium* named 'Joker' that is characterized by its foliage that is variegated with centers that are green-bronze and margins that are bright red with a very thin strip of bronze on the leaf edge, its upright to slightly arching plant habit, and its medium plant height relative to other cultivars of *Phormium*.

2 Drawing Sheets

Botanical classification: *Phormium cookianum*×*Phormium tenax*.

Cultivar designation: 'Joker'.

BACKGROUND OF THE INVENTION

The present invention relates to a new and distinct cultivar of *Phormium* named 'Joker', an interspecific hybrid of *Phormium cookianum*×*Phormium tenax* and referred to hereafter by its cultivar name, 'Joker'. The new cultivar is grown for use as a foliage plant for landscape and container use.

The Inventor discovered the new cultivar summer of 2000 as a naturally occurring chimeral mutation of *Phormium* 'Jester' (not patented) in a container block in his nursery in Auckland, New Zealand.

Asexual propagation of the new cultivar was first accomplished by division in autumn of 2000 in Auckland, New Zealand by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Joker' as a new and unique cultivar of *Phormium*.

1. 'Joker' exhibits foliage that is variegated with centers that are green-bronze and margins that are bright red with a very thin strip of bronze on the leaf edge.
2. 'Joker' exhibits an upright to slightly arching plant habit.
3. 'Joker' exhibits a medium plant height relative to other cultivars of *Phormium*; reaching 60 to 90 cm in height.

'Joker' can be compared to the parent plant, 'Jester'. 'Jester' differs from 'Joker' in having foliage that is variegated with lime-green margins and red-pink centers and paler in overall color (even paler on the lower leaf surface), a smaller plant size, a more arching plant habit, and a slower growth rate. 'Joker' can be most closely compared to the cultivars 'Rainbow Queen' (not patented) and 'Jubilee' (U.S. Plant Pat. No. 19,059). Both are similar to 'Joker' in having leaves with red and green-bronze variegation. 'Rainbow Queen' differs from 'Joker' in having foliage with paler green-bronze centers with a thin paler red-pink margin and in having a more upright plant habit (*P. tenax* habit). 'Jubilee' differs from 'Joker' in having foliage with a lower leaf surface that is more solid red in color and in having a more open and arching plant habit.

BRIEF DESCRIPTION OF THE DRAWING

The accompanying colored photographs illustrate the overall appearance and distinct characteristics of the new *Phormium*. The photographs were taken of a two year-old plant of 'Joker' as grown outdoors in a garden in Auckland, New Zealand.

Figure 1:
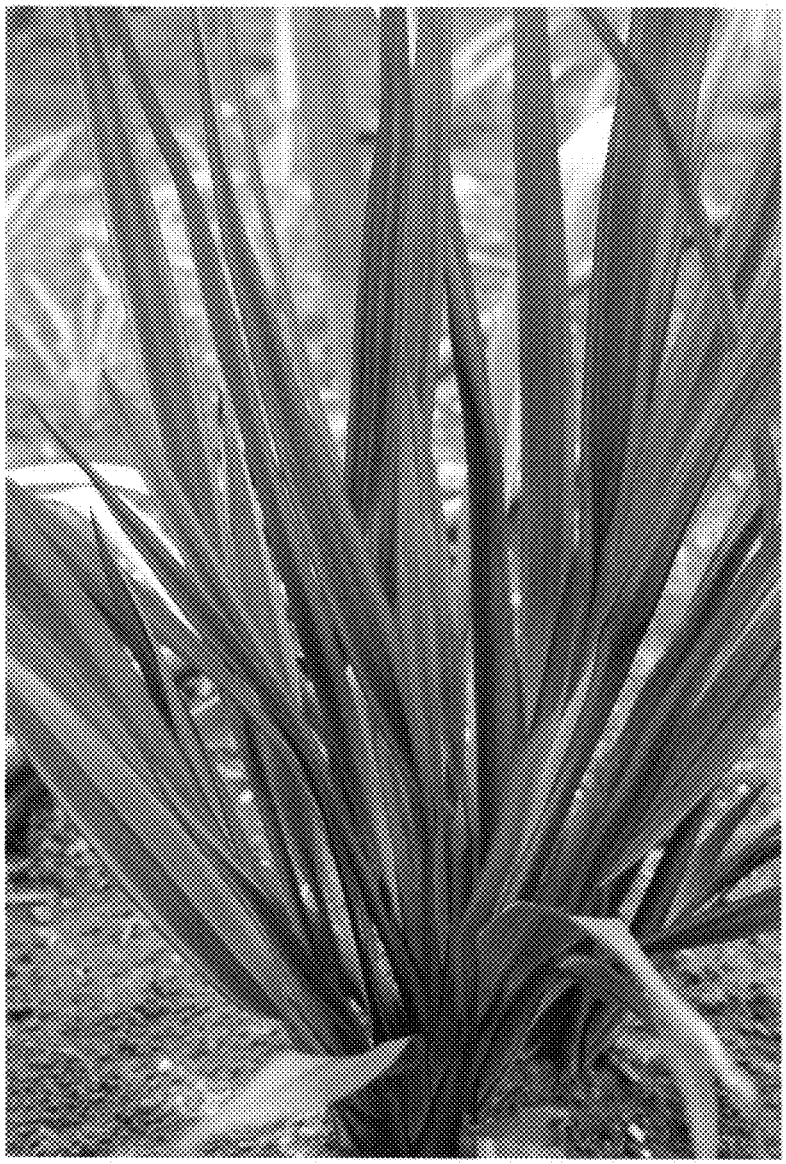
FIG. 1 provides a side view of 'Joker'.
Figure 2:
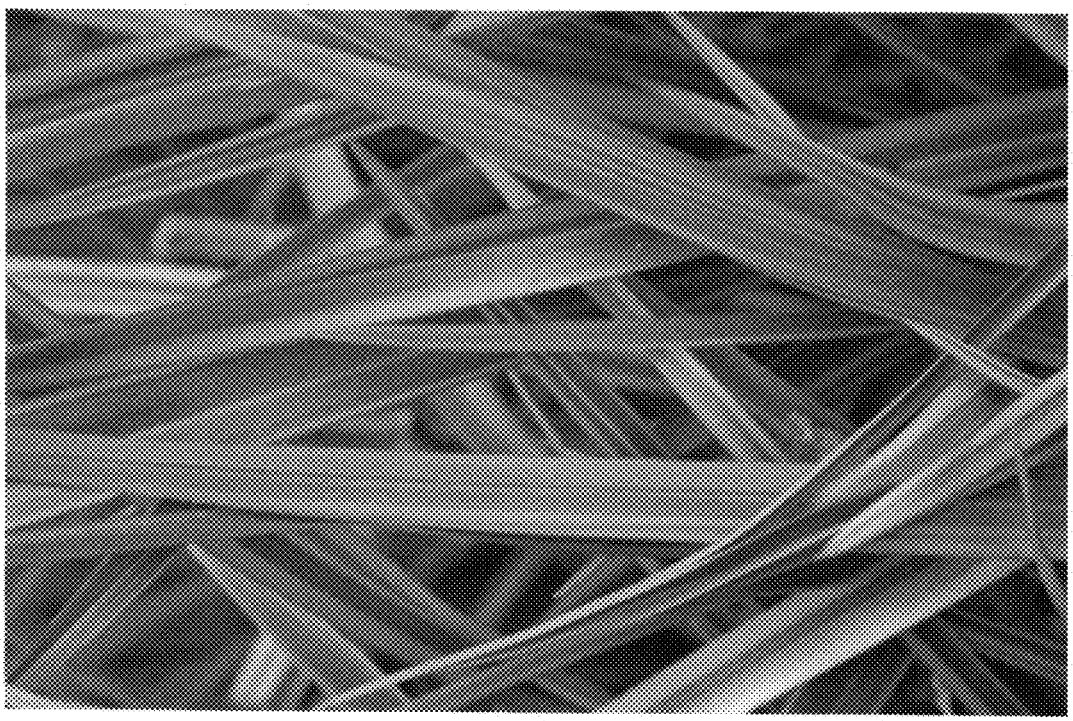
FIG. 2 provides a close-up view of the young foliage of 'Joker'.
Figure 3:
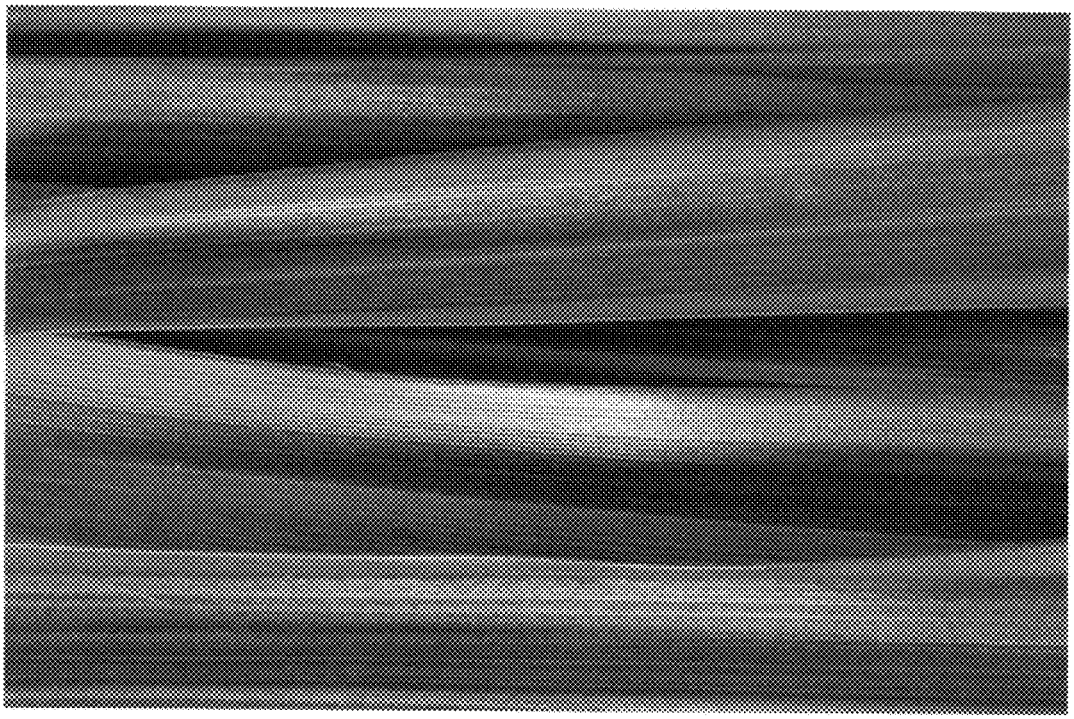
FIG. 3 provides a close-up view of the mature foliage of 'Joker'.

The colors in the photographs may differ slightly from the color values cited in the detailed botanical description, which accurately describe the colors of the new *Phormium*.

DETAILED BOTANICAL DESCRIPTION OF THE PLANT

The following is a detailed description of two year-old plants of the new cultivar as grown outdoors in one gallon containers in Auckland, New Zealand. The plants were grown under average day temperatures of 20° to 27° C. and average night temperatures. of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—No flower production has been observed.

*Plant type*.—Perennial, evergreen.

*Plant habit*.—Clump-forming, upright and slightly arching.

*Height and spread*.—Reaches 60 to 90 cm in height and 30 to 40 cm in width when grown in one gallon containers.

*Hardiness*.—U.S.D.A. Zones 9a to 10b, tolerant to high temperatures of 40° C. and low temperatures of −5° C.

*Diseases and pests*.—No unique susceptibility or resistance to diseases or pests has been observed.

*Root description*.—Fibrous with some larger fleshy roots, 2 to 4 mm in diameter, vigorous, 14D in color.

*Propagation*.—Division.

*Growth rate*.—Moderate with a moderate rate of new fan development (medium in comparison to other cultivars of *Phormium*), produces about 6 new fans from a single fan in 12 months of growth.

*Root development*.—Divisions take 6 to 8 weeks to develop new roots when grown at 20° C.

*Stem description*.—Stem-less, leaves are equitant from base.

Foliage description:

*Leaf shape*.—Lanceolate/Lorate.

*Leaf division*.—Simple.

*Leaf base*.—Sheathed, overlapping.

*Leaf apex*.—Acuminate.

*Leaf venation*.—Parallel, not prominent, same color as leaves, mid rib protruding on lower surface.

*Leaf margins*.—Entire.

*Leaf attachment*.—Sheathed, lacks petioles.

*Leaf arrangement*.—Equitant.

*Leaf number*.—Average of 15 as grown in a 12-cm container.

*Leaf orientation*.—Held upright and becomes slightly arching, moderately concave with medium to sharp keel.

*Leaf substance*.—Stiff, leathery, durable.

*Leaf surface*.—Smooth with fine longitudinal lines, upper surface satiny, lower surface slightly glaucous.

*Leaf color*.—Young leaves upper surface; centers 137A with occasional thin stripes of 58B and 184C, outer edge of leaves 58B and 184C with very thin margins 200C, young leaves under surface; centers dulled N199B with occasional stripes 58B, outer edge of leaves dulled 184B with very thin margins 200C, mature leaves upper surface; centers 137A and 147A with occasional stripes of 58A, outer part of leaves 58B and 184B with very thin margins 200C, mature leaves lower surface; centers: dulled 147A and N199B occasional stripes of 58B and 184C, outer edge of leaves 180A and 58B with a very thin margin 200C.

*Leaf size*.—50 to 90 cm in length and 3 to 4 cm in width.

Flower description: No flowers have been observed to date for the claimed plant.

It is claimed:

1. A new and distinct cultivar of *Phormium* plant named 'Joker' as herein illustrated and described.

* * * * *